(12) United States Patent
Fujisaki et al.

(10) Patent No.: US 6,984,397 B2
(45) Date of Patent: *Jan. 10, 2006

(54) LIPOSOME PREPARATIONS

(75) Inventors: Jiro Fujisaki, Kyoto (JP); Hajime Konno, Takatsuki (JP); Akihiro Kasai, Ikoma (JP); Kazumi Ohtomo, Ibaraki (JP)

(73) Assignee: Fujisawa Pharmaceutical Company, Ltd., Osaka (JP)

( * ) Notice: Subject to any disclaimer, the term of this patent is extended or adjusted under 35 U.S.C. 154(b) by 137 days.

This patent is subject to a terminal disclaimer.

(21) Appl. No.: 10/636,731

(22) Filed: Aug. 8, 2003

(65) Prior Publication Data

US 2004/0028728 A1 Feb. 12, 2004

Related U.S. Application Data

(63) Continuation of application No. 09/926,147, filed as application No. PCT/JP00/01446 on Mar. 10, 2000, now abandoned.

(30) Foreign Application Priority Data

| Mar. 11, 1999 | (JP) | ................................. 11-65469 |
| May 31, 1999 | (JP) | ................................ 11-151866 |

(51) Int. Cl.
*A61K 9/127* (2006.01)

(52) U.S. Cl. ........................ 424/450; 264/4.1; 264/4.3

(58) Field of Classification Search ................ 424/450; 264/4.1, 4.3

See application file for complete search history.

(56) References Cited

U.S. PATENT DOCUMENTS

| 5,089,181 A | 2/1992 | Hauser |
| 5,817,334 A | 10/1998 | Schmidt et al. |

(Continued)

FOREIGN PATENT DOCUMENTS

| EP | 0 530 888 A1 | 3/1993 |
| EP | 0 658 344 A1 | 6/1995 |
| EP | 0 943 327 A1 | 9/1999 |
| EP | 0 562 641 | 9/2003 |
| JP | 9-131348 | 5/1997 |
| JP | 11-046759 | 2/1999 |
| WO | WO 98/24418 | 6/1998 |

OTHER PUBLICATIONS

Waldrep et al., Proceedings of the 6$^{th}$ International Symposium, *Respiratory Drug Delivery VI*, 449-451, May 3-7, 1998.

(Continued)

*Primary Examiner*—Gollamudi S. Kishore
(74) *Attorney, Agent, or Firm*—Leydig, Voit & Mayer, Ltd.

(57) ABSTRACT

The present invention provides a pipecolic acid derivative-containing liposome preparation having has an excellent rapid action capable of coping with an emergent situation such as cerebral infarction.

A liposome preparation characterized by comprising, as an active ingredient, a pipecolic acid derivative of the ingredient described in the present specification or a pharmaceutically acceptable salt thereof entrapped into liposomes, wherein lecithin is mainly used as the liposome-forming lipid, said liposome preparation containing no cholesterol as a stabilizer.

5 Claims, 1 Drawing Sheet

U.S. PATENT DOCUMENTS

| | | |
|---|---|---|
| 6,034,135 A | 3/2000 | Schwartz et al. |
| 6,045,821 A * | 4/2000 | Garrity et al. .............. 424/450 |
| 6,248,363 B1 | 6/2001 | Patel et al. |
| 6,294,192 B1 | 9/2001 | Patel et al. |
| 2002/0012680 A1 | 1/2002 | Patel et al. |
| 2002/0107265 A1 | 8/2002 | Chen et al. |
| 2003/0064097 A1 | 4/2003 | Patel et al. |

OTHER PUBLICATIONS

Van Bommel et al., *International Journal of Pharmaceutics*, 22, 299-310 (1984).

* cited by examiner

LIPOSOME PREPARATIONS

TECHNICAL FIELD

This invention relates to a pharmaceutical liposome preparation comprising, as an active ingredient, a pipecolic acid derivative which attracts special interest lately for its excellent immunosuppressive activity, particularly a macrolide compound, e.g. a tricyclic compound known as tacrolimus (FK506) or a pharmaceutically acceptable salt thereof. More particularly, the present invention relates to a liposome preparation comprising the above active ingredient stably entrapped into liposomes and as a consequence capable of maintaining stable solution in various media such as physiological saline, glucose solution for injection, water or juices and, hence, being applicable to various methods of administration including injections such as intravenous injection, intramuscular injection, and topical injections for intraarticular and the like, topical administration such as application to skin, instillation into eye, nasal administration, and inhalation, and further, oral administration and rectal administration etc. In particular, the present invention relates to a liposome preparation characterized by containing no cholesterol and having a rapid action to such as cerebral ischemic diseases by bolus administration.

BACKGROUND ART

As a liposome preparation containing tacrolimus, for example, there have been known those prepared by incorporating a stabilizer such as cholesterol into phospholipid as a principal ingredient for forming liposome (WO93/08802). With such a constitution, it becomes possible to prepare a liquid preparation from tacrolimus, which is slightly soluble in water. Even if such a preparation is made contacted with a body fluid, crystallization of an active ingredient does not yield so that the preparation exhibits excellent bioavailability and is stable. Therefore, the preparation can take any dosage form represented by injection, instillation into eye, nasal administration, inhalation, percutaneous absorbent, topical injection and the like. Furthermore, it also becomes possible to enhance intensive transmigration of tacrolimus to a site where transmigration of tacrolimus is particularly desired, and to suppress its transmigration to a site where transmigration is not necessarily desired. It is known that excellent effects in practice, such as enhancement of drug efficacy, reduction of side effects and persistence of drug efficacy are obtained as a result.

The liposome preparation exhibits an excellent effect to treatment of cerebral ischemic diseases such as cerebral infarction. However, since a liposome membrane is too stable, the liposome preparation does not exhibit sufficient rapid action, like an anticoagulant, a fibrinolytic agent and a cerebrovascular dilator used as a medical treatment to cerebral infarction. Therefore, it has been required to develop a drug having an excellent rapid action capable of coping with an emergent situation such as cerebral infarction.

An object of the present invention is to improve the problems described above, thereby to provide a pipecolic acid derivative-containing liposome preparation having an excellent rapid action.

DISCLOSURE OF THE INVENTION

The present invention is directed to a liposome preparation comprising, as an active ingredient, a pipecolic acid derivative represented by a macrolide compound of the following general formula (I) or a pharmaceutically acceptable salt thereof entrapped into liposome.

The pipecolic acid derivatives in the present invention means those, which have a common activity capable of having an affinity to FKBP type-immunophilin and inhibiting peptidyl-proryl isomerase and/or rotamase enzyme activity, and which have an common chemical structure capable of being derivatives of pipecolic acid.

Specific example of the pipecolic acid derivatives include a macrolide compound such as tricyclic compound of the following general formula (I) or a pharmaceutically acceptable salt thereof:

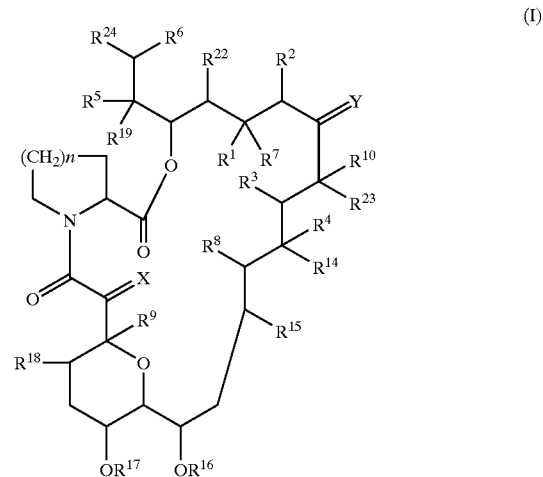

(I)

wherein each of adjacent pairs of $R^1$ and $R^2$, $R^3$ and $R^4$, and $R^5$ and $R^6$ independently:

(a) is two adjacent hydrogen atoms; or (b) may form another bond formed between the carbon atoms to which they are attached; and $R^2$ may also be an alkyl group;

$R^7$ is a hydrogen atom, a hydroxy group, a protected hydroxy group, or an alkoxy group, or an oxo group together with $R^1$;

$R^8$ and $R^9$ are independently a hydrogen atom or a hydroxy group;

$R^{10}$ is a hydrogen atom, an alkyl group, an alkyl group substituted by one or more hydroxy groups, an alkenyl group, an alkenyl group substituted by one or more hydroxy groups, or an alkyl group substituted by an oxo group;

X is an oxo group, a state where a hydrogen atom and a hydroxy group are attached to one carbon atom, a state where two hydrogen atoms are attached to one carbon atom, or a group represented by the formula —$CH_2O$—;

Y is an oxo group, a state where a hydrogen atom and a hydroxy group are attached to one carbon atom, a state where two hydrogen atoms are attached to one carbon atom, or a group represented by the formula =N—NR$^{11}$R$^{12}$ or N—OR$^{13}$;

R$^{11}$ and R$^{12}$ are independently a hydrogen atom, an alkyl group, an aryl group, or a tosyl group;

R$^{13}$, R$^{14}$, R$^{15}$, R$^{16}$, R$^{17}$, R$^{18}$, R$^{19}$, R$^{22}$ and R$^{23}$ are independently a hydrogen atom or an alkyl group;

R$^{24}$ is an optionally substituted heterocyclic ring which may contain one or more hetero atoms; and n represents an integer of 1 or 2.

In addition to the above definitions, Y, R$^{10}$ and R$^{23}$, together with the carbon atoms to which they are attached, may represent a saturated or unsaturated 5- or 6-membered heterocycic ring containing nitrogen, sulfur and/or oxygen atoms, and the heterocyclic ring may be substituted by one or more groups selected from the group consisting of an alkyl, a hydroxy, an alkyloxy, a benzyl, a group of the formula —CH$_2$Se(C$_6$H$_5$), and an alkyl substituted by one or more hydroxy groups.

The definitions used in the above general formula (I) and specific and preferred examples thereof are explained and set forth in detail.

The term "lower" means, unless otherwise indicated, a group having 1 to 6 carbon atoms.

Preferable examples of the "alkyl group" and an alkyl moiety of the "alkoxy group" include a straight or branched chain aliphatic hydrocarbon residue, for example, a lower alkyl group such as methyl, ethyl, propyl, isopropyl, butyl, isobutyl, pentyl, neopentyl and hexyl.

Preferable examples of the "alkenyl group" include a straight or branched chain aliphatic hydrocarbon residue having one double-bond, for example, a lower alkenyl group such as vinyl, propenyl (e.g., allyl), butenyl, methylpropenyl, pentenyl and hexenyl.

Preferable examples of the "aryl group" include phenyl, tolyl, xylyl, cumenyl, mesityl and naphthyl.

Preferable protective groups in the "protected hydroxy groups" and in a "protected amino" described later include 1-(lower alkylthio)(lower)alkyl group such as a lower alkylthiomethyl group (e.g. methylthiomethyl, ethylthiomethyl, propylthiomethyl, isopropylthiomethyl, butylthiomethyl, isobutylthiomethyl, hexylthiomethyl, etc.), more preferably C$_1$–C$_4$ alkylthiomethyl group, most preferably methylthiomethyl group;

tri-substituted silyl group such as a tri(lower)alkylsilyl (e.g., trimethylsilyl, triethylsilyl, tributylsilyl, tert-butyldimethylsilyl, tri-tert-butylsilyl, etc.) or a lower alkyl-diarylsilyl (e.g., methyldiphenylsilyl, ethyldiphenylsilyl, propyldiphenylsilyl, tert-butyldiphenyl silyl, etc.), more preferably tri (C$_1$–C$_4$)alkylsilyl group and C$_1$–C$_4$ alkyldiphenylsilyl group, most preferably tert-butyldimethylsilyl group and tert-butyldiphenylsilyl group; and an acyl group such as aliphatic, aromatic acyl group or aliphatic acyl group substituted by an aromatic group, which are derived from carboxylic acid, sulfonic acid or carbamic acid.

Examples of the aliphatic acyl groups include a lower alkanoyl group optionally having one or more suitable substituents such as carboxy, e.g., formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.;

a cyclo(lower)alkoxy(lower)alkanoyl group optionally having one or more suitable substituents such as lower alkyl, e.g., cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.;

a camphorsulfonyl group; or a lower alkylcarbamoyl group having one or more suitable substituents such as carboxy or protected carboxy, for example, carboxy(lower)alkylcarbamoyl group (e.g., carboxymethylcarbamoyl, carboxyethylcarbamoyl, carboxypropylcarbamoyl, carboxybutylcarbamoyl, carboxypentylcarbamoyl, carboxyhexylcarbamoyl, etc.), tri-(lower)alkylsilyl(lower)alkoxycarbonyl(lower)alkylcarbamoyl group (e.g., trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, tri-methylsilylpropoxycarbonylbutylcarbamoyl, etc.) and the like.

Examples of the aromatic acyl groups include an aroyl group optionally having one or more suitable substituents such as nitro, e.g., benzoyl, toluoyl, xyloyl, naphthoyl, nitrobenzoyl, dinitrobenzoyl, nitronaphthoyl, etc.; and an arenesulfonyl group optionally having one or more suitable substituents such as halogen, e.g., benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.

Examples of the aliphatic acyl groups substituted by an aromatic group include ar(lower)alkanoyl group optionally having one or more suitable substituents such as lower alkoxy or trihalo(lower)alkyl, e.g., phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.

More preferable acyl groups among the aforesaid acyl groups are C$_1$–C$_4$ alkanoyl group optionally having carboxy, cyclo(C$_5$–C$_6$)alkoxy(C$_1$–C$_4$)alkanoyl group having two (C$_1$–C$_4$) alkyls at the cycloalkyl moiety, camphorsulfonyl group, carboxy-(C$_1$–C$_4$)alkylcarbamoyl group, tri(C$_1$–C$_4$) alkylsilyl(C$_1$–C$_4$)alkoxycarbonyl(C$_1$–C$_4$)-alkylcarbamoyl group, benzoyl group optionally having one or two nitro groups, benzenesulfonyl group having halogen, or phenyl (C$_1$–C$_4$)alkanoyl group having C$_1$–C$_4$ alkoxy and trihalo (C$_1$–C$_4$)alkyl group. Among these, the most preferable ones are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl.

Preferable examples of the "saturated or unsaturated 5- or 6-membered heterocyclic ring containing nitrogen, sulfur and/or oxygen atoms" include a pyrrolyl group and a tetrahydrofuryl group.

R$^{24}$ is an optionally substituted heterocyclic ring which may contain one or more hetero atoms, and preferable R$^{24}$ may be cyclo(C$_{5-7}$)alkyl group, and the following ones can be examplified:

(a) a 3,4-di-oxo-cyclohexyl group;

(b) a 3-$R^{20}$-4-$R^{21}$-cyclohexyl group, in which $R^{20}$ is hydroxy, an alkoxy group, an oxo group, or a —$OCH_2OCH_2CH_2OCH_3$ group, and $R^{21}$ is hydroxy, —OCN, an alkoxy group, a heteroaryloxy which may be substituted by suitable substituents, 1- or 2-tetrazolyl, a —$OCH_2OCH_2CH_2OCH_3$ group, a protected hydroxy group, chloro, bromo, iodo, aminooxalyloxy, an azido group, p-tolyloxythiocarbonyloxy, or $R^{25}R^{26}CHCOO$— (in which $R^{25}$ is optionally protected hydroxy or protected amino, and $R^{26}$ is hydrogen or methyl, or $R^{20}$ and $R^{21}$ combine each other to form an oxygen atom in an epoxide ring; or (c) a cyclopentyl group substituted by methoxymethyl, optionally protected hydroxymethyl, acyloxymethyl (in which the acyl moiety optionally contains either dimethylamino group which may be quaternized, or carboxy group which may be esterified), one or more amino and/or hydroxy groups which may be protected, or aminooxalyloxymethyl.

A preferred example is a 2-formyl-cyclopentyl group.

A "heteroaryl which may be substituted by suitable substituents" moiety of the "heteroaryloxy which may be substituted by suitable substituents" may be the ones exemplified for $R^1$ of the compound of the formula I of EP-A-532,088, with preference given to 1-hydroxyethylindol-5-yl, the disclosure of which is incorporated herein by reference.

The tricyclic compounds (I) and its pharmaceutically acceptable salt for use in the present invention are well known to have excellent immunosuppressive activity, antimicrobial activity and other pharmacological activities and, as such, be of value for the treatment or prevention of rejection reactions by transplantation of organs or tissues, graft-vs-host diseases, autoimmune diseases, and infectious diseases with a method of production of them [EP-A-0184162, EP-A-0323042, EP-A-423714, EP-A-427680, EP-A-465426, EP-A-480623, EP-A-532088, EP-A-532089, EP-A-569337, EP-A-626385, WO89/05303, WO93/05058, WO96/31514, WO91/13889, WO91/19495, WO93/04680, WO93/5059, etc.], the disclosures of which are incorporated herein by reference.

Particularly, the compounds which are designated as tacrolimus, FR900520 (ascomycin), FR900523, and FR900525 are products produced by microorganisms of the genus Streptomyces, such as *Streptomyces tsukubaensis* No. 9993 [deposited with National Institute of Bioscience and Human Technology Agency of Industrial Science and Technology (formerly Fermentation Research Institute Agency of Industrial Science and Technology), at 1–3, Higashi 1-chome, Tsukuba-shi, Ibaraki, Japan, date of deposit Oct. 5, 1984, accession number FERM BP-927] or *Streptomyces hygroscopicus* subsp. *yakushimaensis* No. 7238 [deposited with National Institute of Bioscience and Human Technology Agency of Industrial Science and Technology (formerly Fermentation Research Institute Agency of Industrial Science and Technology), at 1–3, Higashi 1-chome, Tsukuba-shi, Ibaraki, Japan, date of deposit Jan. 12, 1985, accession number FERM BP-928][EP-A-0184162]. The tacrolimus of the following chemical formula, in particular, is a representative compound.

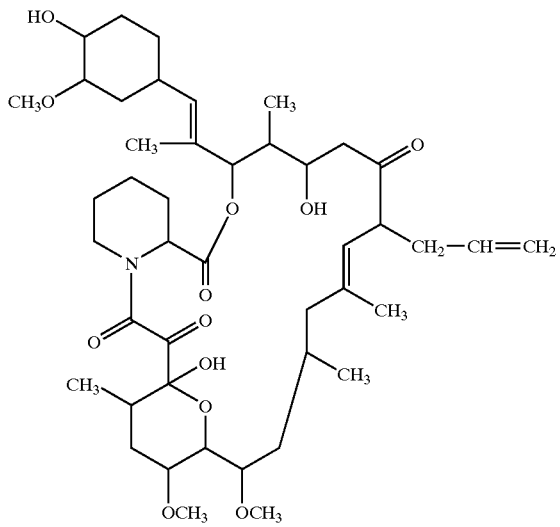

Chemical Name:

17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The preferred examples of the tricyclic compounds (I) are the ones, wherein each of adjacent pairs of $R^3$ and $R^4$, and/or $R^5$ and $R^6$ independently form another bond formed between the carbon atoms to which they are attached;

each of $R^8$ and $R^{23}$ is independently a hydrogen atom;

$R^9$ is a hydroxy group;

$R^{10}$ is a methyl group, an ethyl group, a propyl group or an allyl group;

X is an oxo group, a state where a hydrogen atom and a hydroxy group are attached to one carbon atom, a state where two hydrogen atoms are attached to one carbon atom, or an oxo group;

Y is an oxo group;

each of $R^{14}$, $R^{15}$, $R^{16}$, $R^{17}$, $R^{18}$, $R^{19}$ and $R^{22}$ is a methyl group;

$R^{24}$ is a 3-$R^{20}$-4-$R^{21}$-cyclohexyl group, in which $R^{20}$ is hydroxy, an alkoxy group, an oxo group, or a —$OCH_2OCH_2CH_2OCH_3$ group, and $R^{21}$ is hydroxy, —OCN, an alkoxy group, a heteroaryloxy which may be substituted by suitable substituents, 1- or 2-tetrazolyl, a —$OCH_2OCH_2CH_2OCH_3$ group, a protected hydroxy group, chloro, bromo, iodo, aminooxalyloxy, an azido group, p-tolyloxythiocarbonyloxy, or $R^{25}R^{26}CHCOO$—, in which $R^{25}$ is optionally protected hydroxy or protected amino, and $R^{26}$ is hydrogen or methyl, or $R^{20}$ and $R^{21}$ together form an oxygen atom in an epoxide ring; and n is an integer of 1 or 2.-

The most preferable tricyclic compounds (I) are, in addition to tacrolims, ascomycin derivatives such as halogenated-ascomycin (ASM 981) (e.g., 33-epi-chloro-33-desoxyascomycin), which is disclosed in EP-A-427680, example 66a, 32-O-(1-hydroxyethylindol-5-yl)ascomycin (L-732,531), which is disclosed in EP-A-532088, 32-(1H-tetrazolyl-1-yl)ascomycin (ABT281), which is disclosed in WO93/04680, etc.

As the other preferables examples of the macrolide compounds, rapamycin [THE MERCK INDEX (12th edition), No. 8288] and its derivatives can be examplified. Preferred example of the derivatives is an O-substituted derivative in which the hydroxy in position 40 of formula A illustrateed at page 1 of WO 95/16691 is replaced by —OR$_1$ in which R$_1$ is hydroxyalkyl, hydroalkoxyalkyl, acylaminoalkyl or aminoalkyl; for example,
40-O-(2-hydroxy)ethyl-rapamycin,
40-O-(3-hydroxy)propyl-rapamycin,
40-O-[2-(2-hydroxy)ethoxy]ethyl-rapamycin and
40-O-(2-acetaminoethyl)-rapamycin.

These O-substituted derivatives may be produced by reacting rapamycin (or dihydro or deoxo-rapamycin) with an organic radical attached to leaving group (for example RX where R is an organic radical which is desired as the O-substituent, such as an alkyl, allyl, or benzyl moiety, and X is leaving group such as CCl$_3$C(NH)O or CF$_3$SO$_3$) under suitable reaction conditions.

The conditions may be acidic or neutral conditions, for example in the presence of an acid like trifluoromethanesulfonic acid, camphorsulfonic acid, p-toluenesulfonic acid or their respective pyridinium or substituted pyridinium salts when X is CCl$_3$C(NH)O or in the presence of a base like pyridine, a substituted pyridine, diisopropylethylamine or pentamethylpiperidine when X is CF$_3$SO$_3$.

The most preferable one is 40-O-(2-hydroxy)ethyl rapamycin, which is disclosed in WO94/09010, the disclosure of which is incorporated herein by reference.

The tricyclic compounds (I), and rapamycin and its derivatives, have a similar basic structure, i.e. tricyclic macrolide structure, and at least one of similar biological properties (for example immunosupressive activity).

The pharmaceutically acceptable salt of the tricyclic compound (I), rapamycin and its derivatives may be a conventional non-toxic and pharmaceutically acceptable salt such as salt, with inorganic or organic bases, specifically, an alkali metal salt such as sodium salt and potassium salt, an alkali earth metal salt such as calcium salt and magnesium salt, an ammonium salt and an amine salt such as triethylamine salt and N-benzyl-N-methylamine salt.

With respect to the pipecolic acid derivatives and macrolide compounds used in the present invention, it is to be sunderstood that there may be conformers, and one or more pairs of stereoisomers such as optical isomers due to asymmetric carbon atom(s) and geometrical isomers due to double bond(s), and such conformers and isomers are also included within the scope of the present invention. Furthermore, the pipecolic acid derivatives and macrolide compounds can be in the form of a solvate, which is included within the scope of the present invention. The solvate preferably includes, for example, a hydrate and an ethanolate.

In addition, examples of the pipecolic acid derivatives, which can be used for the object of the present invention, include the followings:

(1) the following Way-124466 compound synthesized by the reaction between 4-phfenyl-1,2,4-triazolin-3,5-dion and rapamycin (Ocain et al., Biochemical and Biophysical Research Communications, Vol. 192, No. 3, 1993);

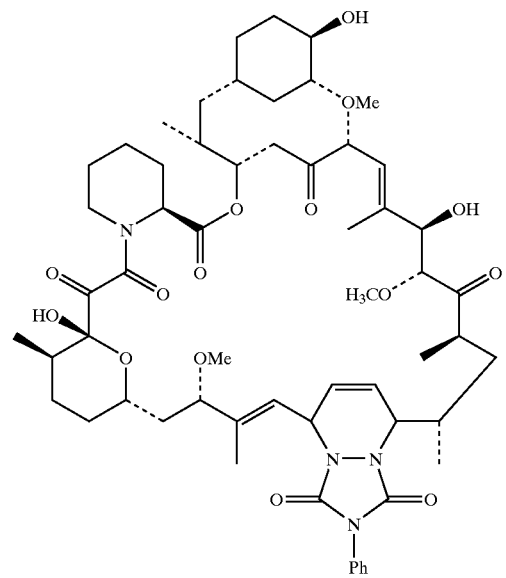

(2) pipecolic acid derivative compound referred to as RAP-Pa (Charkraborty et al., Chemistry and Biology, March 1995, 2: 157–161);

(3) the following pipecolic acid derivative compound (Ikeda et al., J. Am. Chem. Soc. 1994, 116, 4143–4144);

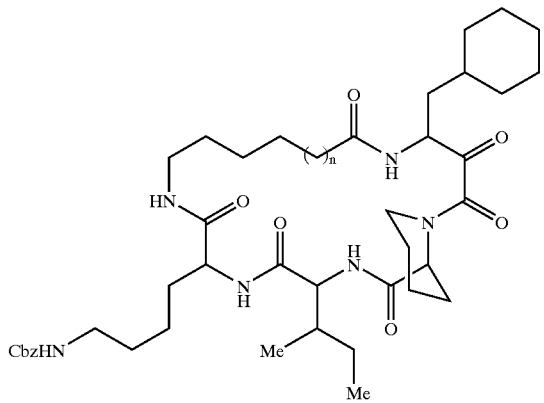

n = 1, 2, or 3

(4) Wang et al., Bioorganic and Medicinal Chemistry Letters, Vol. 4, No. 9, pp. 1161–1166, 1994, particularly pipecolic acid derivative compounds disclosed as the compounds 2a–2d;

(5) the following pipecolic acid derivative (Birkenshaw et al., Bioorganic and Medicinal Chemistry Letters, Vol. 4, No. 21, pp. 2501–2506, 1994);

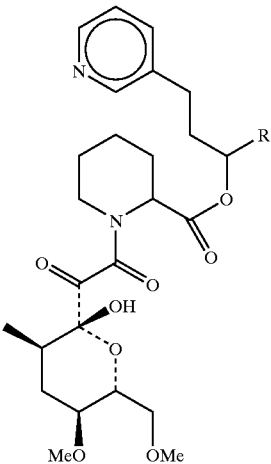

(6) Holt et al., J. Am. Chem. Soc. 1993, 115, 9925–9938, particularly pipecolic acid derivative compounds disclosed as the compounds 4–14;

(7) pipecolic acid derivative compounds disclosed in Caffer et al., Bioorganic and Medicinal Chemistry Letters, Vol. 4, No. 21, pp. 2507–2510, 1994;

(8) pipecolic acid derivative compounds disclosed in Teague et al., Bioorganic and Medicinal Chemistry Letters, Vol. 3, No. 10, pp. 1947–1950, 1993;

(9) Yamashita et al., Bioorganic and Medicinal Chemistry Letters, Vol. 4, No. 2, pp. 325–328, 1994, particularly pipecolic acid derivative compounds disclosed as the compounds 11, 12 and 19;

(10) Holt et al., Bioorganic and Medicinal Chemistry Letters, Vol. 4, No. 2, pp. 315–320, 1994, in particular pipecolic acid derivative compounds disclosed as the compounds 3–21 and 23–24;

(11) Holt et al., Bioorganic and Medicinal Chemistry Letters, Vol. 3, No. 10, pp. 1977–1980, 1993, particularly pipecolic acid derivative compounds disclosed as compounds 3–15;

(12) Hauske et al., J. Med. Chem. 1992, 35, 4284–4296, particularly pipecolic acid derivative compounds disclosed as the compounds 6, 9–10, 21–24, 26, 28, 31–32 and 52–55;

(13) pipecolic acid derivatives disclosed in Teague et al., Bioorganic and Medicinal Chemistry Letters, Vol. 4, No. 13, pp. 1581–1584, 1994; and

(14) Stocks et al., Bioorganic and Medicinal Chemistry Letters, Vol. 4, No. 12, 1457–1460, 1994, particularly pipecolic acid derivative compounds disclosed as the compounds 2, 15–17.

The liposome preparation of the present invention essentially contains the above-described pipecolic acid derivative entrapped into liposomes, and other conditions such as structure, composition, method of production and size of liposomes, and the types of compounds that may be used in combination with liposomes are not specifically limited unless these conditions adversely affect a rapid action of drug and unless these conditions ensure stable entrapping of the pipecolic acid derivatives into liposomes. Thus, the structure of liposome may be a large unilamellar vesicle (LUV), a multilamellar vesicle (MLV) or a small unilamellar vesicle (SUV). Therefore, the size may be within the range from 200 to 1000 nm for LUV, from 400 to 3500 nm for MLV and from 20 to 50 nm for SUV in particle diameter. SUV which exhibits low accumulation into a reticloendothelial system (RES) is preferred.

As the liposome constituting the liposome structure, phospholipids and nitrolipids are used. In general, phospholipids are preferred. Examples thereof include natural phospholipids such as egg yolk lecithin (phosphatidyl choline), soybean lecithin, lysolecithin, sphingomyelin, phosphatidic acid, phosphatidyl serine, phosphatidyl glycerol, phosphatidyl inositol, phosphatidyl ethanolamine, diphosphatidyl glycerol, cardiolipin, plasmalogen, and so on, or hydrogenation products obtainable from said phospholipids by the conventional technology; and synthetic phospholipids such as dicetyl phosphate, distearoylphosphatidyl choline, dipalmitoylphosphatidyl choline, dipalmitoylphosphatidyl ethanolamine, dipalmitoylphosphatidyl serine, eleostearoylphosphatidyl choline, eleostearoylphosphatidyl ethanolamine, eleostearoylphosphatidyl serine and so on, is more preferred ones include lecithins, and the most preferred one is egg yolk lecithin.

Lipids including these phospholipids can be used alone, or two ore more kinds of them can be used in combination. In this case, lipids in which the electronegative group in the phosphatidly group and the electropositive group in the atomic group (ethanolamine, choline and so on) bound thereto are electrically balanced so that the whole molecule is electrically neutral. For example lecithins, sphingomyelin, phosphatidyl ethanolamine, distearoylphosphatidyl choline and so on are often used alone. In contract, lipids which are electronegative as a whole, in which the atopic group (such as serine, glycerol, inositol or the like) combined to the phosphatidyl group (electronegative group) is electrically neutral, for example, phosphatidylserine, phosphatidylglycerol, phosphatidylinositol, and so on or lipids such as phosphatidic acid or dicetyl phosphate which are electronegative, can be used independently as the lipid in this invention, but it is rather recommended that they are used in combination with the neutral lipid such as those mentioned above. Among them, phosphatidic acid and dicetylphosphate do not act as the principal phopholipid in the formation of liposome but are known as liposome-forming additives.

Considering the stability and handling of liposome preparation in the present invention, additives such as excipients and/or stabilizers can preferably be used.

Stabilizers used preferably in the present invention include, for example, stearylamine, α-tocopherol, gangliosides, acidic glycolipid sulfatides; a kind of acidic glycolipid and glycolipids having a sulfuric acid group.

Excipients used preferably in the present invention include, for example, a pharmaceutically acceptable solid saccharide such as monosaccharide (e.g., dextrose, galactose, sorbitol, xylitol, mannitol), disaccharide (e.g., saccharose, lactose, maltose, trehalose), among them lactose and maltose may be more preferably used, especially maltose may be most preferably used.

When liposome is prepared by using cholesterols, a rapid action can be hardly obtained in the same level as that to be required in the present invention and cholesterols are generally likely to exert undesired influence on cerebral infraction. Therefore, cholesterols are not used in the present invention.

It is also possible to use α-tocopherol with expectation of a function for an antioxidant.

A weight ratio of the pipecolic acid derivative to lipid for forming the liposome structure is not specifically limited as far as a liposome preparation capable of exhibiting the desired rapid solubility can be prepared, but is within the range from 1:1 to 1:500, more preferably from 1:5 to 1:100, and most preferably from 1:10 to 1:40.

Considering the stability and handling of liposome preparation in the present invention, a excipient is preferably used. The amount of the excipient is not specifically limited, but the weight ratio of the pipecolic acid derivative to the stabilizer is within the range from 1:10 to 1:1000, more preferably from 1:20 to 1:500, and most preferably from 1:100 to 1:400.

To stabilize the liposome, the amount of the stabilizer to be added is not specifically limited, but the weight percent of the stabilizer to the liposome-forming lipid is preferably within the range from 0.01 to 5%, more preferably from 0.05 to 2%, and most preferably from 0.1 to 1%.

In view of the storage stability, the liposome preparation of the present invention is provided preferably in the form of a dry product (e.g. freeze-dried product) which is free from the solvent, more preferably in the form of solid preparation having a feature that the liposome preparation including a pipecolic acid derivative or a pharmaceutically acceptable salt thereof is dispersed in a pharmaceutically acceptable saccharide as a excipient. Upon use, the liposome preparation is, for example, intravenously injected after being redispersed into a solvent such as distilled water for injection. In case where cerebral ischemic diseases such as cerebral infraction are treated using the preparation of the present invention, intravenous bolus administration or rapid infusion administration is most preferred. The concentration of the pipecolic acid derivative is preferably adjusted within the range from 0.01 to 100 mg/mL, more preferably from 0.05 to 50 mg/mL, and most preferably from 0.1 to 10 mg/mL, after the completion of the redispersion.

On the other hand, the dose of the pipecolic acid derivative to be administered by the liposome preparation of the present invention is appropriately adjusted depending on a kind of the derivative, age of patients, and conditions of diseases to be treated. In case where the pipecolic acid derivative is a tricyclic compound (I), the liposome preparation is preferably administered in a dairy dose within the range from about 0.01 to 1000 mg, preferably from 0.1 to 500 mg, and more preferably from 0.5 to 100 mg.

A particle size of the liposome is not specifically limited as far as the size is within the range of a pharmaceutically acceptable size and in such a range as to exert a rapid action. The size of the liposome can be preferably from 1 to 200 nm, more preferably from 10 to 100 nm, and most preferably from 20 to 80 nm.

If necessary, a filter can be used when an injection cylinder is filled with a liposome preparation redispersed into distilled water for injection. In this case, a conventional filter can be used and preferred example thereof is a sterile, pyrogen-free and a low protein bounding property filter having the pore size of 0.2 μm, 0.22 μm, 0.45 μm, 0.8 μm, or 5 μm (Millipore SLGV025LS, SLHVM25LS, SLAA025LS, SLSV025LS and the like).

The liposome preparation of the present invention can be prepared by the same steps with the following examples.

EXAMPLES

The examples of the present invention will be illustrated but the present invention is not limited to the following examples, and modifications can be made without departing from the purports described hereinabove and hereinafter and are also included in the technical scope of the present invention.

Preparative examples of the compounds of the present invention will be described in detail.

(1) Preparative Example 1 (EtOH injection method): A solution obtained by dissolving purified egg yolk lecithin (20 g) and tacrolimus (1 g) in ethanol (200 mL) is injected and dispersed into a solution obtained separately by dissolving lactose (200 g) in water for injection (1800 mL) with stirring using a homomixer. After filtering the dispersion through a 0.2 μm polycarbonate filter, ethanol in the filtered dispersion was removed by evaporation under reduced pressure and water for injection was added to the dispersion to make a total volume of 2000 mL. The obtained dispersion was filtered through a 0.2 μm polycarbonate filter, each 10 mL of the dispersion was filled into a vial, and then freeze-dried. The resulting freeze-dried liposome preparation was redispersed into 9 mL of water for injection, and a liposome dispersion containing 0.5 mg/mL of tacrolimus and having an average particle diameter of 61.5 nm (measured by a dynamic light scattering method, Model C370 manufactured by NICOMP Co.) was obtained.

(2) Preparative Example 2 (Extrusion method): A solution obtained by dissolving purified egg yolk lecithin (5 g) and tacrolimus (0.25 g) in ethanol (100 mL) is vacuum-dried to form a thin film. This thin film was roughly dispersed into a 10% maltose aqueous solution (500 mL) using a voltex mixer. The dispersion was filtered in turn through 400 nm, 200 nm, 100 nm and 50 nm polycarbonate filters. each 10 mL of the filtrate was filled into a vial, and then freeze-dried. The resulting freeze-dried liposome preparation was redispersed into 9 mL of water for injection, and a liposome dispersion containing 0.5 mg/mL of tacrolimus and having an average particle diameter of 110 nm (measured by a dynamic light scattering method, Model C370 manufactured by NICOMP Co.) was obtained.

(3) Preparative Example 3 (Emulsion method under high pressure): A solution obtained by dissolving purified egg yolk lecithin (20 g) and tacrolimus (1 g) in ethanol (10 mL) vacuum-dried to form a thin film. This thin film was roughly dispersed into a 10% maltose aqueous solution (2000 mL) using a magnetic stirrer. The dispersion was treated using a high-pressure emulsifying machine manufactured by Nanomizer Co. each 10 mL of the resulting liposome emulsion was filled into a vial, and was then freeze-dried. The resulting freeze-dried liposome preparation was redispersed into 9 mL of water for injection, and a liposome dispersion containing 0.5 mg/mL of tacrolimus and having an average particle diameter of 80 nm (measured by a dynamic light scattering method, Model C370 manufactured by NICOMP Co.) was obtained.

(4) Preparative Example 4

In the same manner as in Preparative Example 1, a freeze-dried liposome preparation was obtained from the followin prescriptions and using a suitable amount of water for injection, a liposome dispersion was prepared.

| Tacrolimus | 3 mg |
|---|---|
| Purified egg yolk lecithin | 100 mg |
| Lactose monohydrate | 1000 mg |
| To make | 1103 mg |

(5) Preparative Example 5

In the same manner as in Preparative Example 3, a freeze-dried liposome preparation was obtained from the following prescriptions and using a suitable amount of water for injection, liposome preparations 1) and 2) were prepared.

| 1) | |
|---|---|
| Tacrolimus | 3 mg |
| Purified egg yolk lecithin | 100 mg |
| α-tocopherol | 0.3 mg |
| Maltose | 1000 mg |
| To make | 1103.3 mg |
| 2) | |
| Tacrolimus | 5 mg |
| Purified egg yolk lecithin | 100 mg |
| α-tocopherol | 0.3 mg |
| Maltose | 1000 mg |
| To make | 1105.3 mg |

The test results will be shown below.

A normal rat was anesthetized with halothane. A canula (PE50) was inserted into a femoral vein for administration of a drug. The rat was retained in a fixed cage. After awakening, the drug obtained in the preparative example 3 was administrated over about 30 seconds. Blood samples were collected from an aorta abdominalis of rat under anesthetization with halothane and ice-cooled, and then whole blood was (required amount of about 1 cc) collected. On collection of blood, heparin was added in the amount of 20 μL (about 1000 u/mL) based on 1 mL of whole blood. The blood was stored with freezing until the concentration is measured. With respect to cerebral tissue, cerebrum was removed after decapitation and blood adhered to the periphery of cerebrum was washed and wiped using a filter paper, and then the wet weight of the cerebral was weighted. The cerebrum was put into a centrifugal tube and stored with freezing until the measurement is effected. The cerebral cortex was homogenized with 9 times amount of distilled water as the wet weight of the cerebrum on the day of specimen presentation. The drug concentration of the sample was determined using enzyme immunoassay described in Unexamined Patent Publication (Kokai) No. 1-92659. As is apparent from the results, sufficient concentration in brain or that in blood have been attained within a short period and a sufficient rapid action is exerted. Test results of A the concentration of a tacrolimus-containing liposome preparation in brain and B that in blood are shown in FIG. 1.

BEST MODE FOR CARRYING OUT THE INVENTION

Figure 1A:
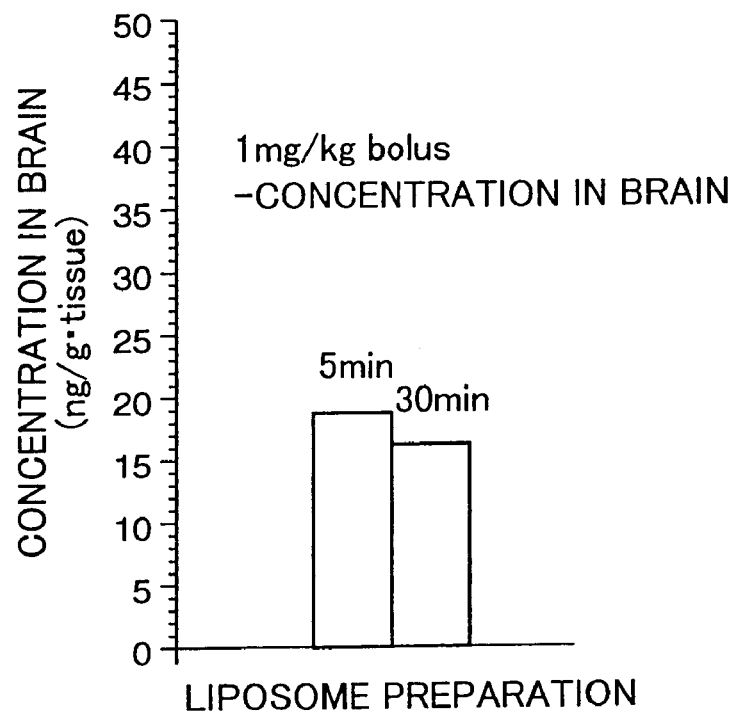
FIG. 1 is a graph showing A the concentration of a tacrolimus-containing liposome preparation in brain and B that in blood.
Figure 1B:
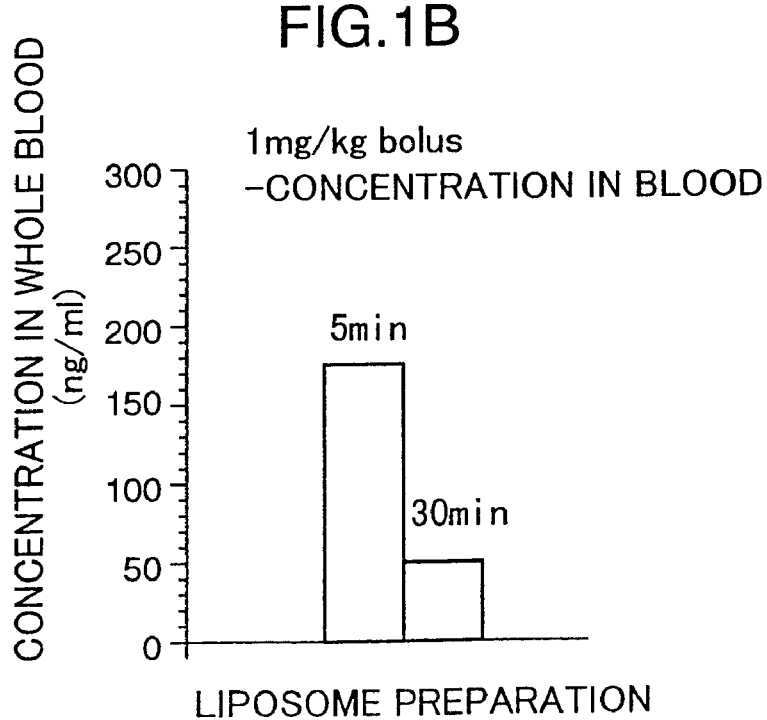

The present invention is directed to a liposome preparation comprising, as an active ingredient, a pipecolic acid derivative represented by a macrolide compound of the following general formula (I) or a pharmaceutically acceptable salt thereof entrapped into liposome.

A liposome preparation containing, as an active ingredient, 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone of the above formula (I) or a pharmaceutically acceptable salt thereof is particularly preferred. With a preferred constitution, lecithin is mainly used as a liposome-forming lipid and the preparation does not contain cholesterol as a stabilizer.

Especially preferable one is in the form of a solid preparation in which a liposome preparation is dispersed in a pharmaceutically acceptable saccharide, the liposome preparation is composed of a liposome containing lecithin as a main component and free from cholesterol, and a pipecolic acid derivative or a pharmaceutically acceptable salt thereof is entrapped in the liposome.

INDUSTRIAL APPLICABILITY

According to the present invention, since liposome can be easily disintegrated as compared with a conventional liposome preparation containing cholesterol, it becomes possible to expect a more excellent rapid action by bolus administration. Furthermore, the preparation of the present invention does not contain a surfactant so that it becomes possible to obtain an excellent effect without exerting any influence on circulatory organs.

Accordingly, the liposome preparation of the present invention is particularly useful for treatment and prevention of diseases wherein a rapid action of drug efficacy is expected, for example, cerebral ischemic diseases (e.g. head injury, hemorrhage in brain (e.g. subarachnoid hemorrhage, intracerebral hemorrhage), cerebral infarction, cerebral thrombosis, cerebral embolism, cardiac arrest, stroke, transient ischemic attack (TIA), hypertensive encephalopathy).

On the basis of the pharmacological effect of a pipecolic acid derivative as an active ingredient, particularly a tricyclic compound (I), the liposome preparation of the present invention is useful for treatment and prevention of the following diseases and conditions:

rejection reactions by transplantation of organs or tissues such as the heart, kidney, liver, bone marrow, skin, cornea, lung, pancreas, small intestine, limb, muscle, nerve, intervertebral disc, trachea, myoblast, cartilage, etc.;

graft-versus-host reactions following bone marrow transplantation;

autoimmune diseases such as rheumatoid arthritis, systemic lupus erythematosus, Hashimoto's thyroiditis, multiple sclerosis, myasthenia gravis, type I diabetes, etc.;

infections caused by pathogenic microorganisms (e.g. *Aspergillus fumigatus, Fusarium oxysporum, Trichophyton asteroides*, etc.);

inflammatory or hyperproliferative skin diseases or cutaneous manifestations of immunologically-mediated diseases (e.g. psoriasis, atopic dermatitis, contact dermatitis, eczematoid dermatitis, seborrheic dermatitis, lichen planus, pemphigus, bullous pemphigoid, epidermolysis bullosa, urticaria, angioedema, vasculitides, erythema, dermal eosinophilia, lupus erythematosus, acne, and alopecia areata);

autoimmune diseases of the eye (e.g. keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Graves' ophthalmopathy, Vogt-Koyanagi-Harada syndrome, keratoconjunctivitis sicca (dry eye), phlyctenule, iridocyclitis, sarcoidosis, endocrine ophthalmopathy, etc.);

reversible obstructive airways diseases [asthma (e.g. bronchial asthma, allergic asthma, intrinsic asthma, extrinsic asthma, and dust asthma), particularly chronic or inveterate asthma (e.g. late asthma and airway hyper-responsiveness) bronchitis, etc.];

mucosal or vascular inflammations (e.g. gastric ulcer, ischemic or thrombotic vascular injury, ischemic bowel diseases, enteritis, necrotizing enterocolitis, intestinal damages associated with thermal burns, leukotriene B4-mediated diseases);

intestinal inflammations/allergies (e.g. coeliac diseases, proctitis, eosinophilic gastroenteritis, mastocytosis, Crohn's disease and ulcerative colitis);

food-related allergic diseases with symptomatic manifestation remote from the gastrointestinal tract (e.g. migrain, rhinitis and eczema);

renal diseases (e.g. intestitial nephritis, Goodpasture's syndrome, hemolytic uremic syndrome, diabetic nephropathy), and nephrotic syndrome (e.g. glomerulonephritis);

nervous diseases (e.g. multiple myositis, Guillain-Barre syndrome, Meniere's disease, multiple neuritis, solitary neuritis, cerebral infarction, Alzheimer's disease, Parkinson's disease, amyotrophic lateral sclerosis (ALS) and radiculopathy);

endocrine diseases (e.g. hyperthyroidism, and Basedow's disease);

hematic diseases (e.g. pure red cell aplasia, aplastic anemia, hypoplastic anemia, idiopathic thrombocytopenic purpura, autoimmune hemolytic anemia, agranulocytosis, pernicious anemia, megaloblastic anemia, and anerythroplasia);

bone diseases (e.g. osteoporosis);

respiratory diseases (e.g. sarcoidosis, pulmonary fibrosis, and idiopathic interstitial pneumonia);

skin diseases (e.g. dermatomyositis, leukoderma vulgaris, ichthyosis vulgaris, photosensitivity, and cutaneous T-cell lymphoma);

circulatory diseases (e.g. arteriosclerosis, atherosclerosis, aortitis syndrome, polyarteritis nodosa, and myocardosis);

collagen diseases (e.g. scleroderma, Wegener's granuloma, and Sjogren's syndrome);

adiposis;

eosinophilic fasciitis;

periodontal diseases (e.g. damage to gingiva, periodontium, alveolar bone or substantia ossea dentis);

male pattern alopecia, alopecia senile;

muscular dystrophy;

pyoderma and Sezary syndrome;

chromosome abnormality-associated diseases (e.g. Down's syndrome);

Addison's disease;

active oxygen-mediated diseases [e.g. organ injury (e.g. ischemic circulation disorders of organs (e.g. heart, liver, kidney, digestive tract, etc.) associated with preservation, transplantation, or ischemic diseases (e.g. thrombosis, cardial infarction, etc.));

intestinal diseases (e.g. endotoxin shock, pseudomembranous colitis, and drug- or radiation-induced colitis);

renal diseases (e.g. ischemic acute renal insufficiency, chronic renal failure);

pulmonary diseases (e.g. toxicosis caused by pulmonary oxygen or drugs (e.g. paracort, bleomycin, etc.), lung cancer, and pulmonary emphysema);

ocular diseases (e.g. cataracta, iron-storage disease (siderosis bulbi), retinitis, pigmentosa, senile plaques, vitreous scarring, corneal alkali burn);

dermatitis (e.g. erythema multiforme, linear immunoglobulin A bullous dermatitis, cement dermatitis);

and other diseases (e.g. gingivitis, periodontitis, sepsis, pancreatitis, and diseases caused by environmental pollution (e.g. air pollution), aging, carcinogen, metastasis of carcinoma, and hypobaropathy)];

diseases caused by histamine release or leukotriene C4 release;

restenosis of coronary artery following angioplasty and prevention of postsurgical adhesions;

autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune orchitis, arthritis (e.g. arthritis deformans), or polychondritis);

ency Virus (HIV) infection, AIDS;

allergic conjunctivitis; and hypertrophic cicatrix and keloid due to trauma, burn, or surgery.

In addition, the macrolide compounds such as tricyclic compound (I) have liver regenerating activity and/or activities of stimulating hypertrophy and hyperplasia of hepatocytes. Therefore, the pharmaceutical liposome preparation of the present invention is useful for increasing the effect of the therapy and/or prophlaxis of liver diseases [e.g. immunogenic diseases (e.g. chronic autoimmune liver diseases such as autoimmune hepatic diseases, primary biliary cirrhosis or sclerosing cholangitis), partial liver resection, acute liver necrosis (e.g. necrosis caused by toxins, viral hepatitis, shock, or anoxia), hepatitis B, non-A non-B hepatitis, hepatocirrhosis, and hepatic failure (e.g. fulminant hepatitis, late-onset hepatitis and "acute-on-chronic" liver failure (acute liver failure on chronic liver diseases))].

And further, the present liposome composition is also useful for increasing the effect of the prevention and/or treatment of various diseases because of the useful pharmacological activity of the said tricyclic macrolides, such as augmenting activity of chemotherapeutic effect, activity of cytomegalovirus infection, anti-inflammatory activity, inhibiting activity against peptidyl-prolyl isomerase or rotamase, antimalarial activity, antitumor activity, and so on.

What is claimed is:

1. A solid preparation comprising a liposome preparation dispersed in a pharmaceutically acceptable saccharide, wherein the liposome preparation comprises liposomes comprising lecithin, wherein the liposomes are free from cholesterol, and the liposomes have tacrolimus or its hydrate entrapped in the liposomes, wherein a mass ratio among tacrolimus or its hydrate, lecithin, and the pharmaceutically acceptable saccharide is 1:1–500:10–1000.

2. The solid preparation as defined in claim 1, wherein the saccharide is lactose or maltose.

3. The liposome preparation as defined in claim 1, which is a freeze-dried product.

4. The solid preparation as defined in claim 1, wherein the liposome preparation further comprises excipients and/or stabilizers.

5. The liposome preparation as defined in claim 1, wherein the liposomes comprise soy phosphatidylcholine.

* * * * *